United States Patent
Savery et al.

(10) Patent No.: US 8,328,721 B2
(45) Date of Patent: Dec. 11, 2012

(54) ULTRASONIC DETERMINATION OF OPTICAL ABSORPTION COEFFICIENTS

(75) Inventors: David Savery, Calries (FR); Ladislav Jankovic, Fishkill, NY (US); Ajay Anand, Fishkill, NY (US)

(73) Assignee: Koninklijke Philips Electronics N.V., Eindhoven (NL)

(*) Notice: Subject to any disclaimer, the term of this patent is extended or adjusted under 35 U.S.C. 154(b) by 727 days.

(21) Appl. No.: 12/442,729

(22) PCT Filed: Sep. 18, 2007

(86) PCT No.: PCT/IB2007/053763
§ 371 (c)(1),
(2), (4) Date: Oct. 13, 2009

(87) PCT Pub. No.: WO2008/038182
PCT Pub. Date: Apr. 3, 2008

(65) Prior Publication Data
US 2010/0043557 A1   Feb. 25, 2010

(30) Foreign Application Priority Data
Sep. 29, 2006   (EP) ................................. 06121524

(51) Int. Cl.
*A61B 8/00* (2006.01)
*A61B 8/15* (2006.01)
(52) U.S. Cl. ........................ 600/437; 600/438; 73/602
(58) Field of Classification Search ............ 73/596, 73/602; 600/407, 437, 438
See application file for complete search history.

(56) References Cited

U.S. PATENT DOCUMENTS

| | | | |
|---|---|---|---|
| 2005/0085725 A1 | 4/2005 | Nagar et al. | |
| 2007/0238958 A1* | 10/2007 | Oraevsky et al. | 600/407 |
| 2009/0105588 A1* | 4/2009 | Emelianov et al. | 600/438 |
| 2012/0150031 A1* | 6/2012 | Castella et al. | 600/431 |

FOREIGN PATENT DOCUMENTS

WO   WO2004086965 A1   10/2004

OTHER PUBLICATIONS

Larina et al, "Real-Time Optoacoustic Monitoring of Temperature in Tissues", Journal of Physics D. Applied Physics, Institute of Physics Publishing Bristol, GB, vol. 38, No. 15, Aug. 7, 2005, pp. 2633-2639, XP020083247.

Anand et al, "Ultrasonic Determination of Three-Dimensional Spatial and Temporal Thermal Distribution for Therapy Monitoring", 2006 IEEE International Conference on Acoustics, Speech, and Signal processing May 14-19, 2006, Toulouse, France, pp. II-1108-II-1111, XP002472118.

(Continued)

*Primary Examiner* — Lisa Caputo
*Assistant Examiner* — Punam Roy

(57) ABSTRACT

A system for the determination of optical coefficients in an object including an ultrasonic scanner for recording first and second pulse echoes before and after the object has been illuminated with a heating light beam from a light source. An evaluation unit determines a map of temperature increase caused by the heating light beam inside the object based on apparent displacements showing up between the second and first pulse echoes.

10 Claims, 4 Drawing Sheets

OTHER PUBLICATIONS

Wilson et. al., "Indirect Versus Direct Techniques for the Measurement of the Optical Properties of Tissues", Photocem Photobiol., 46, 601-608 (1987).

Oraevsky et. el., "Measurement of Tissue Optical Properties by Time-resolved Detection of Laser-induced Transient Stress", Appl. Opt. 36, 402 (1997)).

Seip et al, "Noninvasive Estimation of Tissue Temperature Response to Heating Fields Using Diagnostic Ultrasound", IEEE Transactions on Biomedical Engineering. vol. 42, No. 8, pp. 828-839, 1995).

F. Duck, "Physical Properties of Tissue: A Comprehensive Reference Work", Elsevier Science & Technology Books.

* cited by examiner $$v = v_0 \cdot (1 - \alpha_c \Delta T) \tag{1}$$

$$I^*(x,t) = I(x) \cdot f(t) = I_0 \exp(-\mu_{eff} x) \cdot f(t) \tag{2}$$

$$\mu_{eff} = \sqrt{3\mu_a (\mu_a + \mu_s(1-g))} \tag{3}$$

$$q_{laser} = \int \mu_a(r, \lambda) I(r,\lambda) d\lambda \tag{4}$$

$$q_{laser} = \mu_a(r) I(r,t) \tag{5}$$

$$\rho c \frac{\partial T}{\partial t} = \nabla(k \nabla T) + q_{laser} + q_{pm} \tag{6}$$

$$T(r,t) \propto \exp(-r^2/kt)/(kt)^{3/2} \tag{7}$$

$$\rho c \Delta T = \mu_a \cdot I(r) \cdot t_{laser} \tag{8}$$

$$dt = v(z) \cdot dz \tag{9}$$

$$dt = v_0 \cdot [(z+u(z)+dz+du)-(z+u(z))] \tag{10}$$

$$\frac{v(z)}{v_0} = 1 + \frac{du}{dz} \tag{11}$$

$$\Delta T = -\frac{1}{\alpha_c} \frac{du(z)}{dz} \tag{12}$$

$$\frac{\Delta T(r_A)}{\Delta T(r_B)} = \frac{(\mu_a/\rho c)_A \, I(r_A) t_{laser}}{(\mu_a/\rho c)_B \, I(r_B) t_{laser}} = \frac{I(r_A)}{I(r_B)} = \exp(\mu_{eff}(x_B - x_A)) \tag{13}$$

FIG. 2

ULTRASONIC DETERMINATION OF OPTICAL ABSORPTION COEFFICIENTS

The invention relates to a method, a record carrier, and an examination apparatus for the determination of an optical coefficient, particularly the optical absorption coefficient, at least one measuring location in an object.

The optical absorption and scattering properties of an object comprise valuable information about the material of the object and its chemical composition. In biological tissue, they allow for example to determine functional structures as well as pathophysiological states and regions. Several methods have therefore been proposed to measure the optical absorption coefficient (OAC) inside an object (cf. B. C. Wilson et. al., "Indirect versus direct techniques for the measurement of the optical properties of tissues", Photocem Photobiol., 46, 601-608 (1987); A. A. Oraevsky et. el., "Measurement of tissue optical properties by time-resolved detection of laser-induced transient stress", Appl. Opt. 36, 402 (1997)). Each of these technologies has however specific drawbacks which limit its use in practice.

Based on this background it was an object of the present invention to provide means for the reliable determination of at least one characteristic optical coefficient in an object, particularly of the OAC in biological tissue.

This object is achieved by an examination apparatus according to claim 1, a method according to claim 9, and a record carrier according to claim 13. Preferred embodiments are disclosed in the dependent claims.

The examination apparatus according to the present invention serves for the determination of an optical coefficient, for example of the optical absorption coefficient (OAC) and/or the optical scattering coefficient, at at least one location in an object, wherein said location is called "measuring location" in the following. The apparatus comprises the following components:

- A light source for selectively sending a heating light beam to the measuring location, wherein the term "heating" shall indicate that the light beam induces a temperature increase when it is absorbed by the object. The light source may particularly comprise a laser that allows to generate beams of definite spectral composition and intensity with minimal divergence.
- An ultrasonic scanner for measuring the pulse echoes of ultrasonic pulses which were sent to the measuring location. As is well known to persons skilled in the art, the ultrasonic scanner typically comprises an ultrasound (US) generator for generating US pulses and an US receiver for recording pulse echoes, i.e. the reflections of ultrasonic pulses from structures inside the object. Typically, the US generator and the US receiver are realized by one transducer operating sequentially as generator and receiver.
- An "evaluation unit" for determining the optical coefficient of interest at the measuring location from first and second pulse echoes that were measured before and after a heating light beam was sent to the measuring location, respectively. The evaluation unit is typically realized by a microcomputer with dedicated hardware and/or software. It should be noted that the heating light beam may for example be followed by a period of no light emission during which the second pulse echoes are measured, or that it may for example be continued by a further light beam (particularly with same properties as the heating light beam) which prevails during the measurement of the second pulse echoes.

The examination apparatus allows to determine optical properties of a material with the help of an ultrasonic scanner, wherein the linkage between optical properties and ultrasonic measurement is the generation of heat due to the absorption of light. In particular, this mechanism comprises that the heating light beam will cause a temperature increase in the investigated object that is related to the optical properties of the material, particularly the OAC. This temperature increase will in turn induce changes in the speed of sound in the material which can be detected by the ultrasonic pulse echoes. An advantage of the apparatus resides in the fact that it uses a different physical quality, i.e. (ultra-)sound, that does not directly depend on the optical properties to be measured.

In a preferred embodiment of the invention, the evaluation unit comprises a "temperature mapping module" for determining a spatial map of the temperature increase induced in the object by the heating light beam. A "spatial map" shall by definition refer to a mathematical mapping of a plurality of spatial locations to associated data (e.g. temperature values), wherein said spatial locations may particularly lie on a line or in a two-dimensional area. Preferably the spatial map comprises the complete path of the heating light beam inside the object.

In a further development of the invention, the evaluation unit comprises a "scatter mapping module" for estimating a map of the effective optical scattering properties in the object. The "effective optical scattering properties" typically summarize effects of absorption and scattering of light in the object and therefore determine how much of an incident light beam intensity will reach a target location inside the object. The scatter mapping module is preferably combined with the aforementioned temperature mapping module as the effective optical scattering properties can be inferred from the light-induced temperature increase (e.g. by comparing the temperature increases of adjacent locations with the same optical properties that are successively reached by the heating light beam).

According to another embodiment of the invention, the evaluation unit comprises an "intensity estimation module" for determining the light intensity of the heating light beam at the measuring location. Preferably, said module is further designed such that it allows to determine this intensity not only a one location, but everywhere on the path of the heating light beam through the object. The intensity estimation module is preferably combined with the aforementioned scatter mapping module, as the knowledge of the effective optical scattering properties on the path of the heating light beam can be used to derive the light intensity at each point. It should be noted that, once the light intensity and the temperature increase at the measuring location are known, the optical absorption coefficient there can readily be estimated.

The light emitted by the light source may in principle have any spectral composition. Preferably, the heating light beam emitted by the light source comprises however only light of a given spectral composition, for example monochromatic light that is more or less sharply centered around one particular wavelength. In this case it is possible to investigate the spectral dependency of the optical coefficient of interest and/or to focus on effects that are known to appear at specific wavelengths only.

In the most general setup, the heating light beam and the ultrasonic pulses may be radiated into the object in completely different, independent directions. Preferably, the light source and the ultrasonic scanner are however arranged such that they have parallel emission directions, i.e. that the heating light beam and the ultrasonic pulses travel in the same direction. In this case the measurements of the ultrasonic scanner will immediately reflect the conditions along the path of light propagation which simplifies the calculation of the optical coefficient of interest.

The examination apparatus may further comprise an injection device for injecting a contrast agent with specific light absorbing properties into the object. The injection device may for example comprise a syringe with associated equipment for a definite delivery of contrast agent into the vessel system of a patient. The location of the contrast agent inside the object can then be determined due to its specific optical properties, which allows to identify anatomical structures and/or specific (pathological or healthy) tissue components.

The invention further relates to a method for the determination of an optical coefficient at at least one measuring location in an object, wherein the method comprises the following steps:

Measuring first pulse echoes of ultrasonic pulses sent to the measuring location.

Sending a heating light beam to the measuring location.

Measuring second pulse echoes of ultrasonic pulses sent to the measuring location after the heating light beam has been sent.

Determining the optical coefficient of interest from the first and the second pulse echoes.

The method comprises in general form the steps that can be executed with an examination apparatus of the kind described above. Therefore, reference is made to the preceding description for more information on the details, advantages and improvements of that method.

In a preferred embodiment of the method, the optical coefficient of interest is determined at a plurality of locations inside the object, thus yielding a more or less densely sampled (one-, two- or three-dimensional) spatial map.

In another embodiment of the method, a map of the temperature increase induced by the heating light beam inside the object is determined from the first and second pulse echoes. This temperature increase is directly proportional to the optical absorption coefficient and the light intensity at the considered location.

In a further development of the aforementioned approach, the intensity of the heating light beam is determined at least at the measuring location from the map of temperature increase. Knowing the light intensity that reached the measuring location allows to infer the optical absorption coefficient from the measured temperature increase. The determination of the light intensity at the measuring location may particularly comprise the determination of the effective optical scattering properties on the path of the heating light beam, which can in turn be deduced from a comparison of the temperature increases in small regions with approximately constant optical properties.

Finally, the invention comprises a record carrier, for example a floppy disk, a hard disk, or a compact disc (CD), on which a computer program for the determination of an optical coefficient at at least one measuring location in an object is stored, wherein said program is adapted to execute a method of the aforementioned kind.

These and other aspects of the invention will be apparent from and elucidated with reference to the embodiment(s) described hereinafter. These embodiments will be described by way of example with the help of the accompanying drawings in which:

FIG. 1 shows a principle sketch of an examination apparatus according to the present invention comprising a laser light source, an ultrasonic scanner, and an evaluation unit;

FIG. 2 summarizes mathematical expressions relating to the measurement principle;

Like reference numbers in the Figures refer to identical or similar components.

Figure 1:
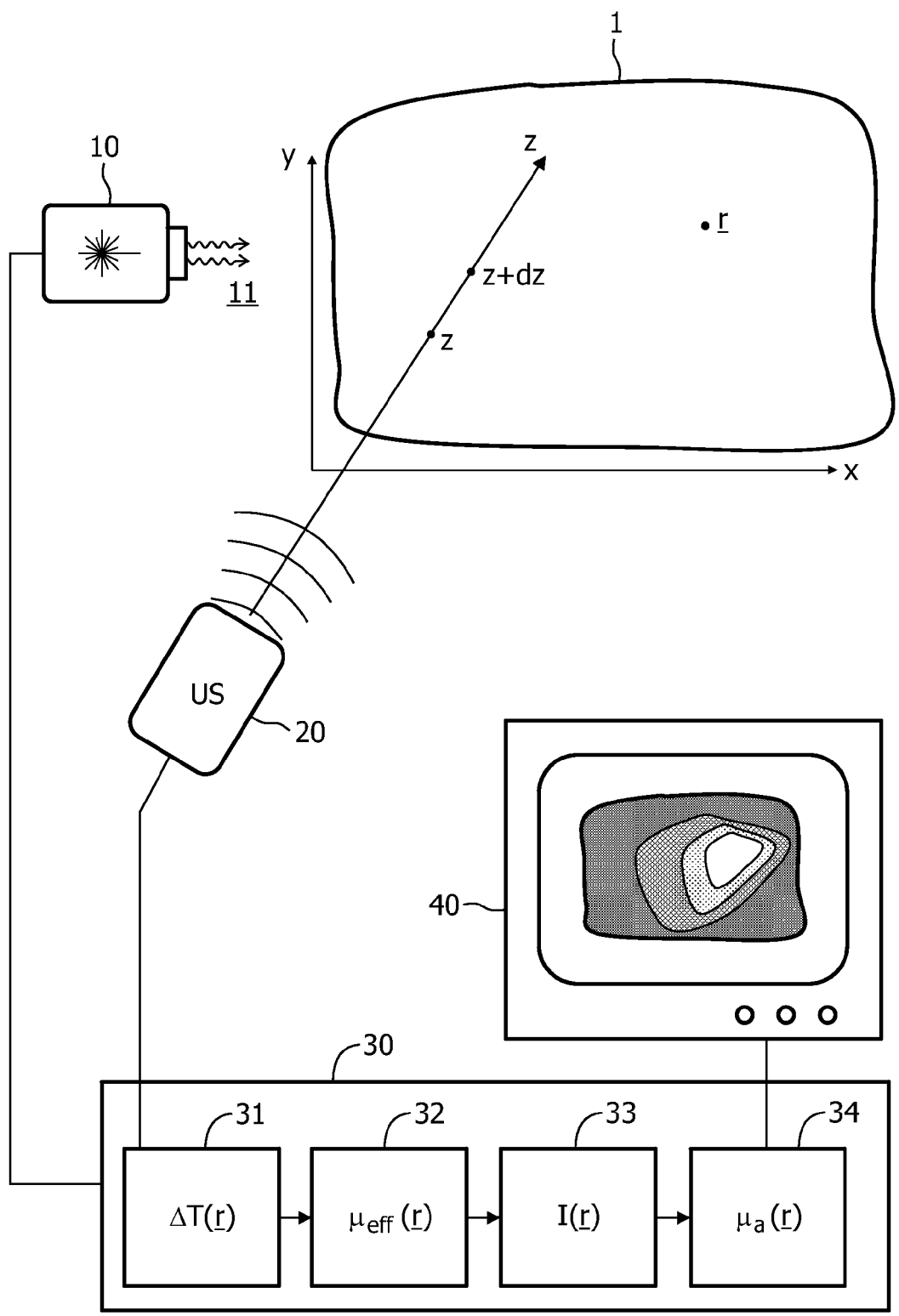

When an optical wave propagates through tissue, it gets both attenuated and scattered. Attenuation, scattering and anisotropy define tissue properties within the diffusion approximation of the radiation transport concept, which describes light propagation under strong scattering conditions. The associated absorption and scattering coefficients are illumination wavelength dependent. Typical optical absorption coefficients (OAC) of a biological tissue for wavelengths in visible and near infrared (NIR) is 2-11 $cm^{-1}$ for muscles, 1-5 $cm^{-1}$ for blood and around 40 $cm^{-1}$ for epidermis. The scattering coefficient is around 140 $cm^{-1}$ for epidermis and 200-500 $cm^{-1}$ for muscles. The OAC is known to give information not only about the nature of tissues, but also about their pathophysiological state (e.g. hemoglobin oxygen saturation, glucose level ($\lambda$=488 nm)). Furthermore, as the wavelength-dependence of the OAC gives a very specific signature of the chemical components present in a medium, a mapping method to image the OAC of biological media could be of major interest for functional imaging. Moreover, with disease-specific optical agents to be injected in blood that absorb particularly specific wavelengths, the OAC of pathological regions can also have an enhanced contrast with respect to the background OAC by using those compounds, enabling imaging in depth. For these reasons, a reliable and feasible method for the measurement of the OAC in an object is highly desirable.

When light, particularly laser light, shall be used to investigate the properties of living tissue, safety regulations have to be observed that dictate maximum allowed laser intensity at a given wavelength. A typical limit is 20 $mJ/cm^2$ per pulse (for ultra-short lasers) or 0.2 $W/cm^2$ for continuous wave (CW) at 532 nm laser wavelength, for instance, and it increases in the infrared wavelength regime reaching 40 $mJ/cm^2$ (per pulse) or 0.4 $W/cm^2$ (CW) at 1064 nm. It should however be noted that the safe use of significantly higher intensities (e.g. two orders of magnitude higher) has been demonstrated for certain applications. The aforementioned figures shall therefore not exclude the use of higher intensities in connection with the present invention.

The aforementioned (allowed) levels of light energy result in a heat deposition of typically a fraction of a Joule per $cm^3$, and a temperature increase of a fraction of one Kelvin to a few Kelvin in an investigated tissue. The heat then gradually diffuses from the laser-absorbing thermal sources to the surrounding tissue. Regarding this light-induced temperature increase, it is known that the speed of sound, v, in biological tissue (with high water content) increases with temperature for temperature rises $\Delta T$ on the order of 10-15 K above normal body temperature (37° C.). For small increases from the normal body temperature ($\Delta T$<10 K), the dependence is nearly linear according to equation (1) of FIG. 2, where $v_0 \cong$ 1540 m/s is the baseline speed of sound at normal body temperature and $\alpha_c$ is in the order of 0.1% $K^{-1}$. This acoustical feature has been used to map a temperature increase from a reference baseline using traditional pulse-echo ultrasonic imaging and elastography-inspired signal processing (cf. R. Seip, E S. Ebbini: "Noninvasive estimation of tissue temperature response to heating fields using diagnostic ultrasound", IEEE Transactions on Biomedical Engineering. Vol. 42, no. 8, pp. 828-839, 1995).

Based on the above considerations, it is proposed here to use pulse-echo ultrasound (PEU) to image a laser-induced temperature increase, and to infer from that temperature increase the OAC inside an object of interest. Assuming that the relation between a map of temperature increase and the OAC distribution is linear in space and time (the laser intensity being supposed to be uniform), PEU has the potential to reconstruct images of the OAC that can bring much information for diagnostic purposes.

FIG. 1 shows a principle sketch of an examination apparatus that realizes the proposed approach. The apparatus is used to investigate the optical properties of an object 1, for example a tissue region under the skin of a patient, wherein an x,y-coordinate system has been drawn for purposes of reference. For simplicity, the following considerations will be limited to a sectional plane through the object, though they may easily be generalized to the three-dimensional case. The examination apparatus comprises the following components:

A laser light source 10 for illuminating the object 1 with a heating light beam 11 propagating along the x-direction.

Figure 4:
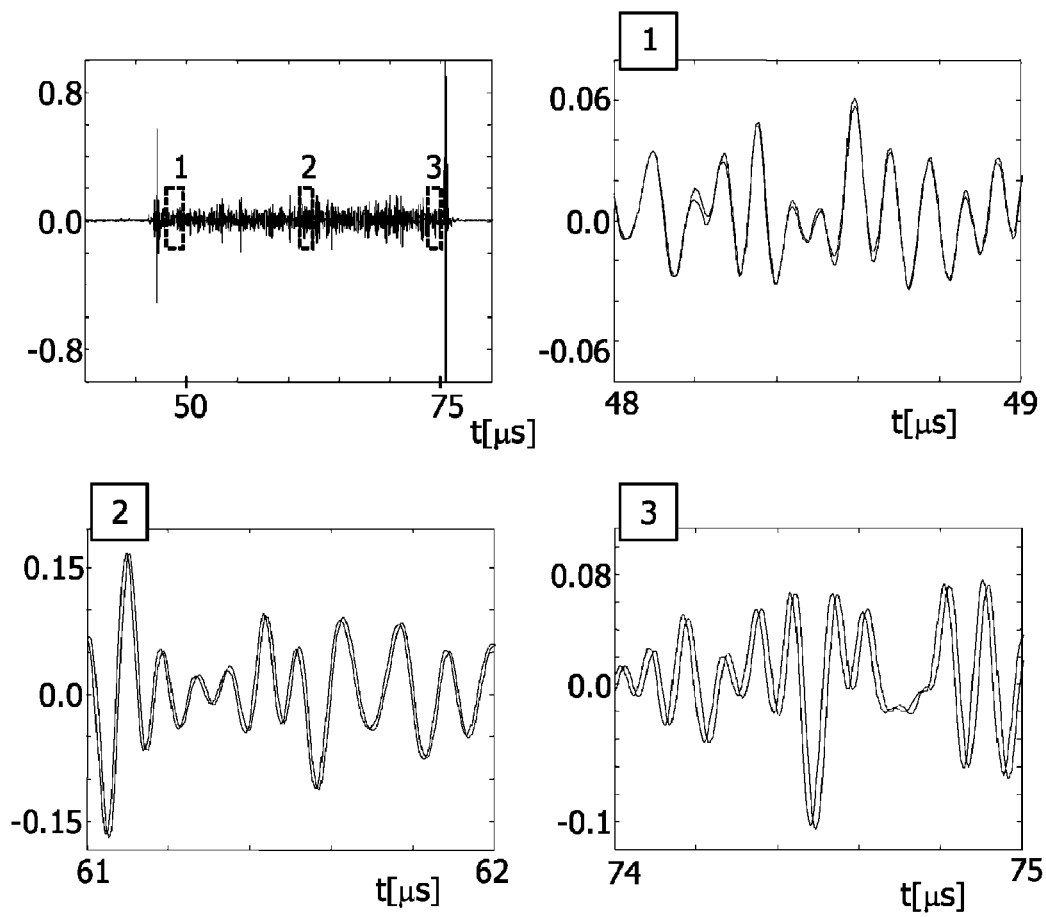
FIG. 4 shows an exemplary pulse-echo waveform in an overview (top left) and in three enlarged windows.

An ultrasonic scanner 20 that emits ultrasonic pulses along a z-direction that can, in the most general case, be diagonal with respect to the x,y-coordinate system and in particular with respect to the direction of light propagation. The US scanner 20 typically comprises an US transducer that first emits an ultrasonic pulse and then records the echoes of this pulse which return from the object after characteristic traveling times (FIG. 4 shows an exemplary pulse-echo waveform recorded by such an ultrasonic scanner).

An evaluation unit 30, for example a workstation, to which the ultrasonic scanner 20 and optionally also the laser light source 10 are coupled. The evaluation unit 30 comprises several modules 31-34 which may be realized by dedicated hardware or, preferably, by suited routines of a computer program.

A display unit 40, for example a computer monitor, for showing measurement results like a map of the determined optical absorption coefficient OAC.

In the following, the basic principles of the proposed measurement approach will be explained with reference to the mathematical expressions summarized in FIG. 2. According to the radiation transport approach, and specifically the diffusion approximation, the intensity $I(x, y)$ of a heating light beam at some depth x within a tissue relates to the incidence intensity $I_0$ at the incidence surface as expressed in equation (2), where it is assumed that the complete spatio-temporal intensity $I^*(x, y, t)$ is a product of a spatial and temporal function and wherein a plane wave configuration is assumed for the spatial part. The effective scattering coefficient $\mu_{eff}$ is defined as in equation (3), wherein $\mu_a$, $\mu_s$ and g are absorption, scattering and anisotropy coefficients, respectively, which are in equation (2) assumed to be constant. For a real tissue they vary spatially and depend on the light illumination wavelength.

The temporal dependence f(t) of the light illumination can be assumed to be instantaneous if the light pulses are temporally much shorter than the temperature diffusion speed. Another extreme is continuous wave illumination, when the diffusion processes after some transition time stabilize and the configuration is in a steady state.

Only a part of an incident light beam with intensity $I(r)$ at a position $r=(x, y)$ within the tissue (cf. FIG. 1) is absorbed, wherein the absorbed energy density $q_{laser}$ is proportional to the optical absorption coefficient (OAC) $\mu_a$. Considering absorption and illumination spectral properties in addition to their spatial distribution, the absorbed energy $q_{laser}$ is given by equation (4), which is in the following approximated by equation (5). Due to the absorbed energy density $q_{laser}$, each absorption centre will behave as a heat source.

The temperature distribution $T(r, t)$ resulting from these heat sources can be derived from the bioheat equation (6), where $\rho$ is the density, c the specific heat, k the heat conductivity, $q_{laser}$ the light absorption term and $q_{pm}$ a term that contains effects from perfusion and metabolic activity. For short time scales, the last term $q_{pm}$ does not play an important role and can be neglected. Solving this equation for the case of a single spherical absorbing particle positioned within a non-absorbing tissue gives the temperature distribution of equation (7), assuming that the time t is large enough so that there is an ongoing heat diffusion process.

For short heating times, smaller than the characteristic diffusion times of tissue (which are on the order of seconds), the heat transfer equation (6) can be simplified to equation (8), in which $t_{laser}$ represents the time the laser was on and $\Delta T$ represents the induced temperature rise. Knowing the values of $\rho$ and c for the tissue type under consideration (e.g. from F. Duck: "Physical Properties of Tissue: A Comprehensive Reference Work", Elsevier Science & Technology Books), the laser on-time $t_{laser}$, the laser intensity $I=I(r)$ at the measuring location r, and the temperature rise $\Delta T$ (measured from ultrasonic data), the optical absorption coefficient $\mu_a$ can be obtained from equation (8). In the following, it will therefore be explained how the missing data can be determined, i.e. (i) the temperature rise $\Delta T$ and (ii) the laser intensity $I(r)$.

When a region of tissue is heated, the resulting temperature change $\Delta T$ results in variations in the speed of sound. As a result, the backscattered ultrasound echoes (at radio-frequency RF) from the heated region undergo time shifts, and these time shifts can be mapped into apparent displacements u assuming a nominal constant speed $v_0$ of sound throughout the medium (typically 1540 m/s). In the following, it will be assumed that the apparent displacements will only depend on the direction z of propagation of the ultrasound beam, i.e. $u=u(z)$. The time dt that an US pulse needs to travel form a location z to the location z+dz (cf. FIG. 1) is described by equation (9). This time dt is interpreted by the US receiver as being caused by a travel of the sound with a constant speed $v_0$ from a shifted location z+u(z) to a shifted location z+u(z)+dz+du, see equation (10). Combining equations (9) and (10) yields equation (11), from which equation (12) can be derived with the help of equation (1). The dimensionless quantity du(z)/dz is referred to as "temperature-induced strain" as it is the spatial gradient of an apparent displacement. This temperature-induced strain is measured from the ultrasound RF backscatter data in a way well-known to persons skilled in the art. Pulse echo speckle measurements can thus be used to obtain a temperature map $\Delta T(r)$ of the tissue.

In addition, the pulse echo provides the tissue geometry and structure. The tissue geometry/structure and its temperature rise map $\Delta T(r)$ are further sufficient to create an optical absorption and scattering map. To this purpose, the ratio of temperature increases at two nearby locations $r_A=(x_A, y_A)$, $r_B=(x_B, y_B)$ is considered in equation (13), wherein it is assumed that the material coefficients $\mu_a$, $\rho$, c are approximately the same at the two locations (e.g. if $r_A$ and $r_B$ are chosen from the same type of tissue). Thus the effective scattering coefficient $\mu_{eff}$ that appears in equation (2) can be derived from the measured temperature increases $\Delta T(r_A)$, $\Delta T($ $r_B$) and the measured distance ($x_B-x_A$). Repeating this procedure for the whole object yields a map $\mu_{eff}(\underline{r})$ of effective scattering coefficients.

In the next step, the intensity $I(\underline{r})$ of a heating light beam that arrives at a location r can be determined by integration of a generalized equation (2) with the help of the now known effective scattering coefficients $\mu_{eff}(\underline{r})$.

Finally, the OAC $\mu_a$ at location r can be directly calculated from equation (8) as now both $\Delta T$ and $I(\underline{r})$ are known.

The described basic steps of the optical absorption mapping procedure can readily be expanded to a multi-layer tissue case by repeating the basic procedure for different transducer positions. An especially simplistic case is when the laser illumination comes from the transducer side (i.e. light propagation is along the pulse-echo line z in FIG. 1). Since the pulse-echo provides inherently depth information (and thus separation between the locations $r_A$ and $r_B$ considered above), it is not required to know the tissue geometry/structure to find OAC tissue map.

Figure 3:
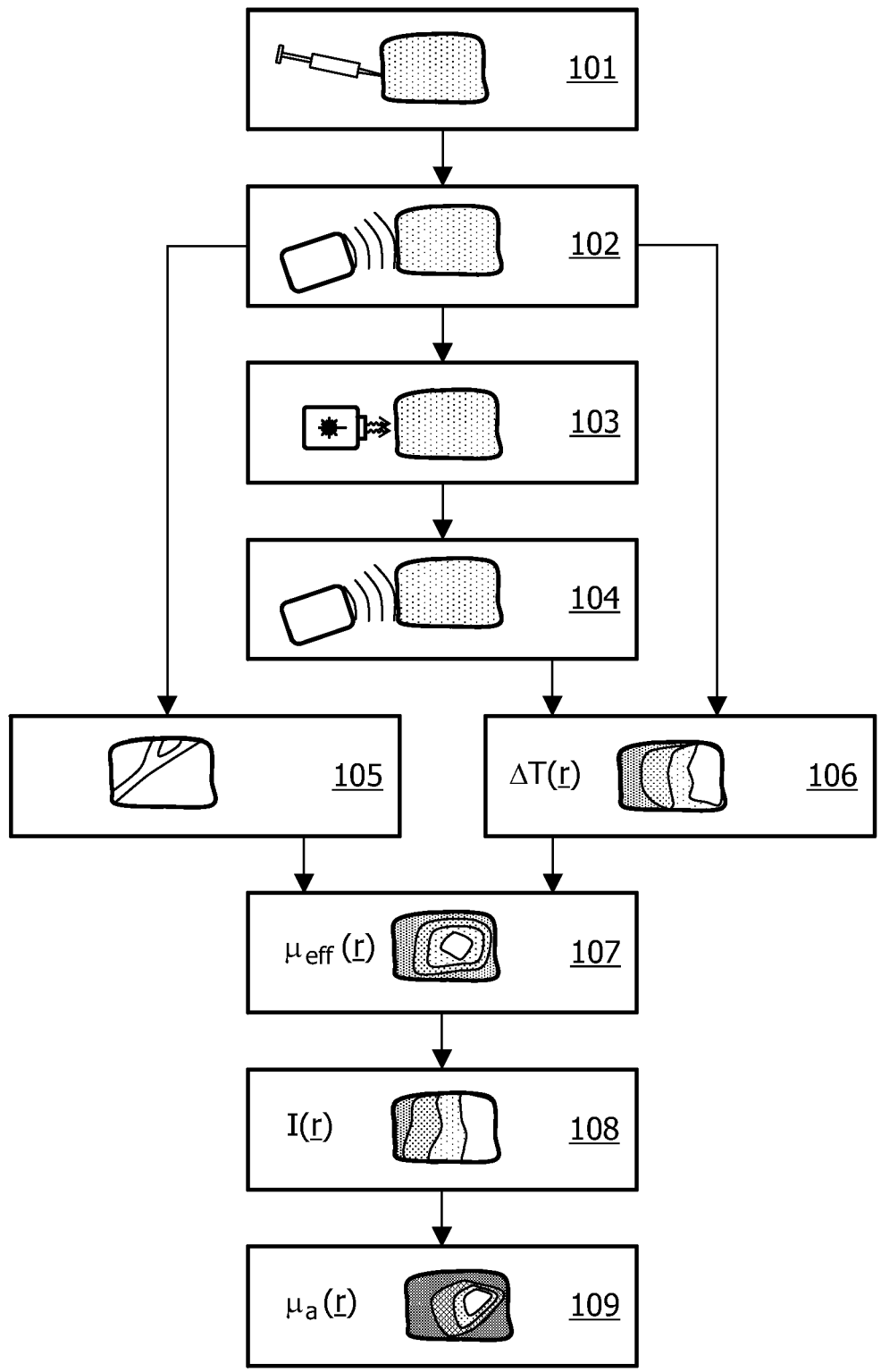
FIG. 3 is a flow diagram of a typical examination procedure for the determination of the optical absorption coefficient in an object.

FIG. 3 shows the flow diagram of a typical measurement procedure with the examination apparatus of FIG. 1 based on the principles explained above. The procedure starts at step 101 with an optional injection of a photoactive substance as a contrast agent into the body volume of interest. The contrast agent may particularly be targeting some specific tissue inside a patient. Examples of possible contrast agents are indocyanine green (ICG) and nanoparticles.

In the next step 102, a first pulse-echo signal is recorded with the ultrasonic scanner 20, from which a body structure image can optionally be determined in step 105.

After recording of the first pulse echoes, the object is illuminated with a heating laser light beam of initial intensity $I_0$ for the pulse duration $t_{laser}$ in step 103. The heating light beam will induce an associated temperature increase $\Delta T$ in the illuminated regions of the object. Immediately after the illumination, a second image of pulse echoes is recorded with the ultrasonic scanner 20 in step 104. This image is preferably generated with the same imaging parameters (position of scanner, frequency, viewing angle etc.) as the first pulse-echo image of step 102.

The temperature-induced strain du/dz that is found in the second pulse-echo image with respect to the first pulse-echo image is evaluated in step 106 according to equation (12) to derive the local temperature increases $\Delta T(\underline{r})$. This step 106 is performed in a "temperature mapping module" 31 of the evaluation unit 30 shown in FIG. 1.

In the next step 107, the temperature map $\Delta T(\underline{r})$ and optionally also the structural image obtained at step 105 is used to determine a map $\mu_{eff}(\underline{r})$ of effective scattering coefficients according to equation (13). This step 107 is performed in a "scatter mapping module" 32 of the evaluation unit 30.

Based on the map $\mu_{eff}(\underline{r})$ of effective scattering coefficients, the light intensity distribution $I(\underline{r})$ throughout the object can be determined in step 108 based on the given initial light intensity $I_0$ and the direction of the heating light beam according to equation (2). This step 108 is performed in an "intensity mapping module" 33 of the evaluation unit 30.

In a final step 109, the desired map $\mu_a(\underline{r})$ of the OAC is determined with the help of equation (8) from the intensity $I(\underline{r})$ and the temperature increase $\Delta T(\underline{r})$ previously obtained. This step is performed in an "OAC mapping module" 34 of the evaluation unit 30. Additionally or alternatively to the OAC, other optical coefficients like the scattering coefficient $\mu_s$ could be determined as well.

In summary, the described method for acquiring optical absorption coefficients from ultrasonic pulse-echo images comprises the following basic steps:

1) An ultrasonic pulse-echo image is acquired before and shortly after the light illumination exposure, wherein one pulse-echo line before and after illumination can be sufficient for obtaining the OACs along the line.
2) The temperature change is identified in at least two spatially separated points which belong to a tissue section sharing the same OAC.
3) The optical absorption coefficient is obtained from the temperature change ratio between the aforementioned points and their separation, combined with at least one of the temperature changes and its depth information. The minimum required separation of the relevant points is only determined by the temperature acquiring process resolution.

Figure 5:
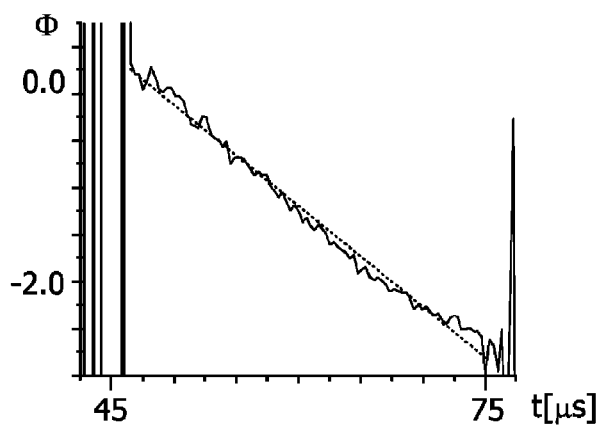
FIG. 5 shows the phase-shift in dependence on the depth inside an object determined from the data of FIG. 4.

FIG. 4 shows exemplary pulse-echo waveforms obtained from an ink doped agar gel phantom of block-shape immersed into water (vertical axis: relative units; horizontal axis: pulse traveling time t). The ink was uniformly dispersed during the phantom fabrication process. Pulsed, nanosecond Nd:YAG, laser was shined from a side of the phantom, providing uniform illumination along the ultrasonic pulse-echo acquisition line as the US transducer was aligned along an edge of the phantom perpendicular to the light direction (corresponding to an axis z perpendicular to the x-axis in FIG. 1). In the shown captured echo from the phantom (top left diagram), two signals—before and after laser illumination—are strongly overlapped and can be resolved only after zooming-in as shown in the graphs 1, 2 and 3. According to these graphs 1, 2 and 3, the after illumination signal has a phase (time) shift (corresponding to the apparent displacement u considered above). Since the phase shift is cumulative, the after the illumination signal overlaps the before the illumination signal in the window 1 (graph 1), and gradually separates from it at larger depths (windows 2 and 3). The laser illumination is uniform along the phantom surface, resulting in a uniform temperature change. Therefore the phase shift increases/decreases linearly. FIG. 5 shows in this respect a nearly linear drop in phase shift $\Phi$ (vertical axis) along the length of the phantom (horizontal axis, measured by the pulse traveling time t). Using equation (12), this corresponds to a 2 K temperature increase (assuming $\alpha_c=0.001$ for the phantom) in the phantom following application of the laser pulse. The slope of the curve, $d\Phi/dt=-\alpha_c\omega_0\Delta T$ (with $\omega_0=2\pi\cdot 10$ MHz), indicates a temperature rise in the phantom on the order of 1.7 K for a heated zone of 2 cm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An examination apparatus for the determination of an optical coefficient of at least one measuring location in an object, the examination apparatus comprising:
   a light source for selectively sending a heating light beam to the measuring location;
   an ultrasonic scanner for emitting ultrasonic pulses and measuring pulse echoes of the ultrasonic pulses sent to the measuring location; and
   an evaluation unit for determining the optical coefficient at the measuring location from pulse echoes that were measured before and after sending a heating light beam to the measuring location, wherein the evaluation unit comprises at least one of a temperature mapping module for determining a spatial map of the temperature increase induced in the object by the heating light beam and a scatter mapping module for estimating a spatial map of the effective optical scattering properties in the object.

2. The examination apparatus according to claim 1, wherein the evaluation unit comprises an intensity estimation module for determining the light intensity of the heating light beam at the measuring location.

3. The examination apparatus according to claim 1, wherein the optical coefficient comprises the optical absorption coefficient and/or the optical scattering coefficient.

4. The examination apparatus according to claim 1, wherein the heating light beam comprises only light of a given spectral composition.

5. An examination apparatus for the determination of an optical coefficient of at least one measuring location in an object, the examination apparatus comprising:
   a light source for selectively sending a heating light beam to the measuring location;
   an ultrasonic scanner for emitting ultrasonic pulses and measuring pulse echoes of the ultrasonic pulses sent to the measuring location; and
   an evaluation unit for determining the optical coefficient at the measuring location from pulse echoes that were measured before and after sending a heating light beam to the measuring location,
   wherein the light source and the ultrasonic scanner have parallel radiation directions.

6. An examination apparatus for the determination of an optical coefficient of at least one measuring location in an object, the examination apparatus comprising:
   a light source for selectively sending a heating light beam to the measuring location;
   an ultrasonic scanner for emitting ultrasonic pulses and measuring pulse echoes of the ultrasonic pulses sent to the measuring location;
   an evaluation unit for determining the optical coefficient at the measuring location from pulse echoes that were measured before and after sending a heating light beam to the measuring location; and
   an injection device for injecting a contrast agent with specific light absorbing properties into the object.

7. A method for the determination of an optical coefficient at of at least one measuring location in an object, comprising:
   emitting a plurality of ultrasonic pulses to the measuring location;
   measuring first pulse echoes of the ultrasonic pulses sent to the measuring location;
   sending a heating light beam (11) to the measuring location;
   measuring second pulse echoes of the ultrasonic pulses sent to the measuring location;
   determining the optical coefficient from the first and second pulse echoes; and
   determining at least one of a map of temperature increase inside the object from the first and second pulse echoes and an estimate of a spatial map of the effective optical scattering properties in the object.

8. The method according to claim 7, wherein the optical coefficient is determined at a plurality of locations inside the object.

9. The method according to claim 7, wherein the method comprises the act of determining at least one of a map of temperature increase inside the object from the first and second pulse echoes, wherein the intensity of the heating light beam at the measuring location is determined from the map of temperature increase.

10. A non-transitory record carrier on which a computer program for the determination of an optical coefficient at of at least one measuring location in an object is stored, said program when executed by a processor configuring the processor to control an examination apparatus to execute a method comprising acts of:
   emitting a plurality of ultrasonic pulses to the measuring location;
   measuring first pulse echoes of the ultrasonic pulses sent to the measuring location;
   sending a heating light beam to the measuring location;
   measuring second pulse echoes of the ultrasonic pulses sent to the measuring location;
   determining the optical coefficient from the first and second pulse echoes; and
   determining at least one of a map of temperature increase inside the object from the first and second pulse echoes and an estimate of a spatial map of the effective optical scattering properties in the object.

* * * * *